United States Patent [19]

Kolombos et al.

[11] 4,392,003
[45] Jul. 5, 1983

[54] ISOBUTENE BY DEHYDROISOMERIZATION OF NORMAL BUTANE

[75] Inventors: Alexander J. Kolombos, Thames Ditton; Clive D. Telford, Ascot; Dennis Young, Staines, all of England

[73] Assignee: The British Petroleum Company Limited, London, England

[21] Appl. No.: 271,429

[22] Filed: Jun. 8, 1981

[30] Foreign Application Priority Data

Jun. 12, 1980 [GB] United Kingdom ............... 8019241

[51] Int. Cl.$^3$ .................. C07C 5/24; C07C 5/32; C07C 5/40
[52] U.S. Cl. .................. 585/661; 585/654; 585/671; 585/751; 252/455 Z
[58] Field of Search ............ 585/661, 654, 671, 734, 585/739, 748, 666, 660, 662, 663, 664; 252/455 Z

[56] References Cited

U.S. PATENT DOCUMENTS

| 2,389,406 | 11/1945 | Bloch et al. | 585/671 |
|---|---|---|---|
| 3,804,746 | 4/1974 | Chu | 585/654 |
| 4,056,576 | 11/1977 | Gregory et al. | 585/654 |
| 4,304,686 | 12/1981 | Telford | 252/455 Z |
| 4,324,940 | 4/1982 | Dessau | 585/666 |
| 4,329,516 | 5/1982 | AlMuddarris | 585/661 |

FOREIGN PATENT DOCUMENTS

| 737533 | 6/1966 | Canada | 585/671 |
|---|---|---|---|
| 24930 | 3/1981 | European Pat. Off. | 585/671 |
| 1507549 | 4/1978 | United Kingdom | 585/671 |

OTHER PUBLICATIONS

Choudbury, Chemical Industry Developments, 8, 32 (1974), A Review, only relevant pages enclosed.
Egloff et al., J. Am. Chem. Soc., 61, 3571 (1939).

Primary Examiner—Delbert E. Gantz
Assistant Examiner—A. Pal
Attorney, Agent, or Firm—Brooks, Haidt, Haffner & Delahunty

[57] ABSTRACT

This invention relates to a method of dehydroisomerizing n-butane by contacting at elevated temperatures a feedstock containing n-butanes with a catalyst composition containing a gallium compound on a support. The process affords a valuable method of producing isobutene which is a basic chemical feedstock for a number of products including polyisobutenes, methacrolein and methyl tertiary butyl ether, to name a few. The last named compound can be prepared by reacting isobutene with methanol and is a convenient means of separating iso-butene from the products of the dehydroisomerization stage.

8 Claims, No Drawings

ISOBUTENE BY DEHYDROISOMERIZATION OF NORMAL BUTANE

The present invention relates to a process for producing isobutene by dehydro-isomerisation of normal butane.

Isobutene is a valuable raw material in the petrochemical industry, and many commercial processes have been developed using isobutene as starting material. For example, isobutene can be:

(a) oxidised catalytically to produce methacrolein and methacrylic acid;
(b) ammoxidised to produce methacrylonitrile;
(c) hydrated to produce tertiary butyl alcohol;
(d) reacted with formaldehyde to produce isoprene (modified Prins reaction);
(e) reacted with methanol to produce methyl teriary butyl ether which is a valuable gasoline blending component for high octane motor fuels;
(f) used as an alkylating agent either as such or in the form of its halogenated derivatives; and
(g) used as a monomer which can be homo-polymerised to a wide variety of polyisobutenes or copolymerised with a range of other monomers to produce a selection of rubbery materials.

Hitherto, the only routes available to meet this enormous demand for isobutene for the aforementioned uses have been by converting the more readily available normal butane to isobutene in a two-stage process. The two stages are those of isomerisation and dehydrogenation. For example normal butanes can be isomerised to isobutane by the catalyst and process disclosed in our British Pat. Nos. 953187 and 953189 respectively. The isobutane thus produced may then be dehydrogenated to the isobutene according to the process disclosed for example in our British Pat. No. 1507549. Alternatively, normal butane may first be dehydrogenated to normal butene and then subsequently isomerised by known techniques as disclosed for example in our British Pat. Nos. 1065006 and 1065010, to the corresponding isobutene. The catalysts, reaction conditions and the recovery techniques needed for each of these stages are different and this places an economic penalty on the composite two-stage process for producing isobutene from normal butane.

Our earlier British Pat. Nos. 1507549, 1507778, 1533169 and 1537780 also describe the use of gallium compounds on various supports for the conversion of $C_3$–$C_8$ hydrocarbons to a variety of products including olefins, oligomers and aromatics. Moreover, our British Pat. No. 1561590 also claims and describes the use of gallium compounds in combination with aluminosilicates having a high silica to alumina ratio for the conversion of light hydrocarbons into aromatics. Such zeolites containing a high silica to alumina ratio are typified by high acidity as shown by a number of tests, for example the α-test as described in a letter to the editor entitled "Superactive Crystalline Aluminosilicate Hydrocarbon Cracking Catalysts", by Weisz, P. B. and Miale, J. N. in the Journal of Catalysis, Vol. 4, pp. 527–529 (August 1965). The α-value of the support is an indication of its hexane cracking activity.

It has now been found that by using a catalyst composition in which the support has a low acidity, n-paraffins can be dehydroisomerised to iso-olefins in a single step and n-olefins can be isomerised directly to iso-olefins.

It is an object of the present invention to devise an integrated single stage process for dehydro-isomerising normal butanes to isobutenes by selecting a catalyst which is capable of carrying out both stages in one reaction.

It is a further object of the present invention to select a catalyst which not only dehydro-isomerises normal butane to isobutene but is also capable of isomerising normal butene to isobutene.

Accordingly, the present invention is a process for the dehydroisomerisation of a hydrocarbon feedstock containing normal butanes to isobutenes which comprises bringing the hydrocarbon feedstock at an elevated temperature into contact with a catalyst composition comprising an element from Group IIIa of the Periodic Table or a compound thereof in combination with a support of α-value below 45.

The Group IIIa of the Periodic Table referred to herein is the Table appearing on pp. 448 and 449 of the Handbook of Chemistry and Physics, Ed. by Hodgman, M. S. et al. and published by the Chemical Rubber Publishing Company, Ohio, USA (1961, reprinted 1963).

The hydrocarbon feedstock containing normal butanes may be derived from any of the well-known sources. For example the source of n-butane feed may be the by-products from a petroleum refining process from which the $C_1$ to $C_3$ fraction and the $C_5$ and higher fractions have been separated. An alternative source of n-butane feed may be gas fields and/or associated gas.

The Group IIIa element or a compound thereof used in the catalyst for the dehydro-isomerisation process of the present invention is preferably a gallium compound, suitably gallium oxide. The gallium compound is preferably deposited on a support selected from an alumina, a silica and a silicate, e.g. a zeolite, including those with very low aluminium content such as for example silicalite, metal tectosilicates or boralites, or gallium ions are exchanged for cations already present in the support. The concentration of gallium in the catalyst composition is suitably between 0.05% and 20%, preferably between 0.2% and 3.0% by weight of the support.

The low acidity support preferably has an α-value below 30. Such supports can also be characterised by their inability to convert methanol into hydrocarbons rich in aromatics below 500° C. Examples of such supports include aluminosilicate zeolites; zeolites in which the framework aluminium is at least partially replaced by other metals; silicalites; tectosilicates and boralites. The aluminosilicates which fall into this class usually have a low number of acid sites, i.e. low alumina content although those with a relatively high alumina content but in which the site acid activity is low may also be used. Examples of such aluminosilicates are listed in Tables I and II. An example of silicalite is Silicalite-2, described by Bibby, D. M. et al. in Nature, Vol. 280, No. 5724, pp. 664–665 (1979). Metal tectosilicates e.g. gallosilicates of low acidity can be used. Examples of boralites are typified in an article entitled "Molecular Sieve Borosilicates", by Taramasso, M., Berego, G. and Notari, B. in the Proceedings of the Fifth International Conference on Zeolites, Naples, 1980, pp. 40–48, Edited by Rees, L. V. C. and published by Heyden and Son Limited, London 1980. Those silicates which have a relatively high acidity can be converted to the low acidity type by well known deactivation processes including steaming and selective coking.

The dehydro-isomerisation reaction is carried out by passing the hydrocarbon feedstock in the vapour phase over the catalyst maintained at an elevated temperature. The catalyst is suitably maintained at a temperature above 200° C., preferably at a temperature between 350° and 700° C.

The isobutene may, if desired, be recovered from the dehydroisomerisation reaction products by any suitable separation process either physical or chemical. For example, some of the chemical reactions are very selective towards isobutene. A typical example is the reaction between isobutene and methanol to form methyl tertiary butyl ether. In this case the product of the dehydro-isomerisation reaction may be reacted with methanol directly without any preliminary separation of the isobutene and, when the reaction is complete, the product is water washed to remove excess methanol and the organic phase containing the product ether, normal butane, isobutane and normal butenes is flash-distilled to recover as overheads the paraffins and normal olefins and as bottoms the methyl tertiary butyl ether. In view of the versatile nature of the dehydro-isomerisation catalyst of the present invention, the overheads thus recovered may be recycled directly to the dehydro-isomerisation stage without any further separation thereby providing a very simple process for producing methyl tertiary butyl ether from a feedstock which predominantly contains normal butanes.

It is believed that the dehydro-isomerisation process of the present invention proceeds through a transient intermediate stage wherein normal butenes are produced (together with some isobutane) which are then subsequently isomerised. Under those circumstances, there must be an equilibrium stage between the amount of normal butenes present and the amount of isobutenes present both in the reactant and in the products. Therefore, by controlling the amount of catalyst used in the process it will be possible to influence the amount of a particular isomer formed in the product. It is for this reason that the feed to the dehydro-isomerisation process can be a mixture of isomers such as that which is recycled after the separation of methyl tertiary butyl ether.

If the dehydro-isomerisation process of the present invention is used as a part of the integrated process for producing methyl tertiary butyl ether from hydrocarbon feedstock rich in normal butanes, the dehydroisomerisation catalyst of the present invention offers a further advantage in that it is capable of converting some of the $C_4$ hydrocarbons in the feed to aromatics. In view of the fact that methyl tertiary butyl ether is generally used as a gasoline blending component, the presence of aromatics will incidentally enhance the blending characteristics of the ether and also improve the octane value of the gasoline with which it is blended.

The process of the present invention is further illustrated with reference to the following Examples.

In the Examples, the n-butane was passed over the specified catalyst for approximately 10 minutes (Examples 1, 2, 7, 8) or 30 minutes (Examples 3-6) at the given temperatures and contact times and at atmospheric pressure. The amount of isobutene present in the total yield of mixed butene formed was approximately 33% by weight.

Notes on the Table III (1) Ga-aluminosilicate catalyst made according to Example 1 of the published European Pat. application No. 0024930A1.
(2) Ga-aluminosilicate catalyst from the same batch as Note 1 was steam deactivated in situ by passing over water vapour (0.2 mol/h) in air (76.2 ml/h, STP) at 570° C. for 10 hours then dried under dry air (76.2 ml/h, STP) for 3 hours at 570° C. prior to passing over butane as in Example 6.

TABLE I

EFFECT OF $SiO_2:Al_2O_3$ ON HEXANE CRACKING OF SELECTED ALUMINOSILICATE ZEOLITES

| Material | $\dfrac{SiO_2}{Al_2O_3}$ (molar) | α |
|---|---|---|
| H-ZSM-5 | 28 | 680 |
|  | 40 | 480 |
|  | — | 400 |
|  | 70 | 177 |
|  | 140 | 125 |
|  | 220 | 100 |
|  | 500 | 37 |
| H-ZSM-11 | 870 | 2.1 |
|  | 1516–2880 | 0.3–0.7 |
| H-ZSM-48 | Ca- | S |
|  | 395 | 6.4 |
| H-ZSM-24 (3) | 8.5 | 22.9 |

All materials in acid form

TABLE II

EFFECT OF OTHER FRAMEWORK METALS ON α

| Structure Type | $\dfrac{SiO_2}{Al_2O_3}$ | $\dfrac{SiO_2}{M_2O_3}$ | α |
|---|---|---|---|
| "ZSM-5" | 4762 | 53.2 (Cr) | 0.04–0.06 |
|  | 555 | 30.9 (Fe) | 0.75–1.73 |
|  | 909 | 30.3 (Fe) | 0.13–0.34 |
| "ZSM-12" | 256 | 1111 (Cr) | 61–67 |
|  | 833 | 3333 (Cr) | 2.1 |
|  | 909 | 175 (Cr) | 0.4–0.6 |

All materials in acid form

TABLE III

| Example No | Feed | Catalyst | Reaction Temperature °C./contact time/s | Conversion wt % | Yield (wt %) Aromatics | Yield (wt %) Butene | Selectivity to butenes wt % |
|---|---|---|---|---|---|---|---|
| 1 | n-butane | Ga—Zeolite L | 550/6 | 55 | 2.5 | 28.9 | 49.0 |
| 2 | n-butane | Ga—SiO$_2$ | 500/6 | 16 | 1.6 | 8.6 | 53.8 |
|  |  |  | 590/6 | 56 | 6.6 | 22.0 | 39.3 |
|  |  |  | 650/6 | 82 | 8.2 | 14.8 | 26.8 |
| 3 | n-butane | Ga—Silicalite (I) | 570/1.6 | 33 | NIL | 8.5 | 25.5 |
| 4 | n-butane | Ga—Erionite | 570/1.6 | 18 | NIL | 5.8 | 32.7 |
| 5* | n-butane | Ga—aluminosilicate (1) | 535/1.6 | 99 | 59.0 | 0.3 | 0.3 |
| 6 | n-butane | Ga—aluminosilicate (2) | 570/1.6 | 58 | 8.3 | 9.2 | 16.0 |
| 7 | iosbutane | Ga—Al$_2$O$_3$ | 550/6 | 52 | 15.8 | 17.0 | 32.7 |

TABLE III-continued

| Example No | Feed | Catalyst | Reaction Temperature °C./contact time/s | Conversion wt % | Yield (wt %) Aromatics | Butene | Selectivity to butenes wt % |
|---|---|---|---|---|---|---|---|
| 8 | isobutane | Ga—SiO$_2$ | 590/6 | 65 | 9.2 | 39.0 | 60.0 |

*comparative test using high acidity support (not according to the invention)

EXAMPLE 9

The crystalline gallosilicate was prepared in the following manner. 0.85 g of δ-Ga$_2$O$_3$ was added to a solution of 2.6 g NaOH in 25 g of deionised water and the resulting mixture heated to 80° C. On complete dissolution of the oxide, the solution was filtered and allowed to cool to room temperature (Solution A). 60.4 g of 200% w/w aqueous tetrapropylammonium hydroxide solution was added to a mixture of 27 g of deionised water and 75 g of Ludox AS40 (Registered Trade Mark) colloidal silica (Solution B). Solution A was added to Solution B with rapid stirring for 15 minutes. 80 ml of the resultant mixture was heated in a sealed 100 ml capacity stainless steel bomb at 140° C. for 60 hours. The water washed and dried product was calcined at 580° C. for 16 hours then refluxed twice with 0.67 M aqueous NH$_4$NO$_3$ solution each for 1 hour then gallium loaded and bound in silica as in European patent application No. 0024930 A1.

| Example No | 9 |
|---|---|
| Feed | n-butane |
| Catalyst | Ga—Gallosilicate |
| Reaction Temperature °C./ Contact Time (sec) | 569/1.0 |
| Conversion wt % | 39.7 |
| Yield Aromatics wt % | 3.3 |
| Butene | 11.3 |
| Selectivity to Butenes | 28.9 |

We claim:

1. A process for dehydroisomerisation of a hydrocarbon feedstock containing normal butane to isobutene which comprises bringing the feedstock at an elevated temperature into contact in a single stage with a catalyst composition comprising an element from Group IIIa of the Periodic Table or a compound thereof in combination with a support of α-value below 45, said support being a zeolite selected from the group consisting of an aluminosilicate, a silicalite, a metal tectosilicate, and a boralite.

2. A process according to claim 1 wherein a gallium compound is deposited on a support.

3. A process according to claim 2 wherein the gallium compound is gallium oxide.

4. A process according to claim 1 wherein gallium ions from a gallium compound are exchanged with cations on the support.

5. A process according to claims 1, 2, 3, or 4 wherein the concentration of gallium in the catalyst composition is between 0.05 and 20% by weight of the support.

6. A process according to preceding claims 1, 2, 3, or 4 wherein the dehydroisomerisation reaction is carried out by passing the feedstock in the vapour phase over the catalyst composition maintained at a temperature between 350° and 700° C.

7. A process according to claims 1, 2, 3, or 4 wherein the isobutene formed is separated from the dehydroisomerisation reaction products by conversion thereof into methyl tertiarybutyl ether.

8. A process according to claim 7 wherein the conversion to methyl tertiarybutyl ether is achieved by reacting the dehydroisomerisation products with methanol.

* * * * *

UNITED STATES PATENT AND TRADEMARK OFFICE
CERTIFICATE OF CORRECTION

PATENT NO. : 4,392,003

DATED : July 5, 1983

INVENTOR(S) : ALEXANDER J. KOLOMBOS, CLIVE D. TELFORD and DENNIS YOUNG

It is certified that error appears in the above—identified patent and that said Letters Patent is hereby corrected as shown below:

Col. 4, line 39, under the heading "Material" in Table I, "H-ZSM-24(3)" should read --H-ZSM-25(3)--.

Signed and Sealed this

Twenty-fourth Day of January 1984

[SEAL]

Attest:

GERALD J. MOSSINGHOFF

Attesting Officer

Commissioner of Patents and Trademarks